(12) United States Patent
Wright et al.

(10) Patent No.: US 6,784,160 B1
(45) Date of Patent: Aug. 31, 2004

(54) BIOLOGICALLY ACTIVE PREGNENE COMPOUNDS

(75) Inventors: Amy E. Wright, Fort Pierce, FL (US); John K. Reed, Fort Pierce, FL (US); Ross E. Longley, Tallahassee, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 10/410,335

(22) Filed: Apr. 9, 2003

Related U.S. Application Data

(60) Provisional application No. 60/371,379, filed on Apr. 9, 2002.

(51) Int. Cl.[7] .......................... A61K 31/70; C07H 3/00
(52) U.S. Cl. ............................................. 514/26; 536/5
(58) Field of Search ................. 536/5; 514/26

(56) References Cited

U.S. PATENT DOCUMENTS 6,093,805 A * 7/2000 Shull et al. .................. 536/4.1

OTHER PUBLICATIONS

Cimino, G. et al. "Chemistry of Mediterranean gorgonians, II. Pregna 4, 20–dien–11α–of–ol–3–one acetate, a novel steroid from the gorgonian *Eunicella cavolini*" *Experientia* 1979, vol. 35, p. 298.

Cobar, O.M. et al. "A new steroidal glycoside from a Caribbean gorgonian, Eunicea sp. 1" *J. Nat. Prod.* 1997, vol. 60, pp. 1186–1188.

Faulkner, D.J. "Marine Natural Products" *Nat. Prod. Rep.* 2000, vol. 17, pp. 7–55.

Faulkner, D.J. "Marine Natural Products" *Nat. Prod. Rep.* 2001, vol. 18, pp. 1–49.

Faulkner, D.J. "Marine Natural Products" *Nat. Prod. Rep.* 2002, vol. 19, pp. 1–48.

Kingston, J.F. et al. *J. Chem. Soc., Perkin Trans. I* 1979, vol. 1, p. 2064.

Long, B.H. et al. "Eleutherobin, a novel cytotoxic agent that induces tubulin polymerization, is similar to paclitaxel (Taxol)" *Cancer Res.* 1998, vol. 58, pp. 1111–1115.

Ross, R.A., Scheuer, P.J. "18–Acetoxy– and 18–Hydroxypregna–1, 4, 20–Trien–3–one from the Telestacean Octocoral *Telesto Riisei*" *Tetrahedron Lett.* 1979, p. 4701.

Scheuer, P.J. (ed) *Marine Natural Products, Chemical and Biological Perspectives*, Academic Press, New York, 1978–1983, vol. I–V.

* cited by examiner

Primary Examiner—Elli Peselev
(74) Attorney, Agent, or Firm—Saliwanchik, Lloyd & Saliwanchik

(57) ABSTRACT

The subject invention provides novel compositions of biologically active glycosylated pregnene compounds which can advantageously be used for treating cancer and stopping cell proliferation.

9 Claims, 1 Drawing Sheet

BIOLOGICALLY ACTIVE PREGNENE COMPOUNDS

CROSS-REFERENCE TO A RELATED APPLICATION

This application claims the benefit of provisional patent application Ser. No. 60/371,379, filed Apr. 9, 2002, which is hereby incorporated by reference in its entirety.

FIELD OF THE INVENTION

This invention relates to organic compounds and compositions which have useful therapeutic properties. More particularly, the invention concerns novel pregnene compounds having anti-proliferative and antitumor activities, pharmaceutical compositions comprising such compounds, and methods of their use for therapeutic purposes.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed. Anti-proliferative agents can also be useful in treating autoimmune diseases and inflammatory disease.

In searching for new biologically active compounds, it has been found that some natural products and organisms are potential sources for chemical molecules having useful biological activity of great diversity. For example, the diterpene commonly known as paclitaxel, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Paclitaxel is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine soft corals have also proven to be a source of biologically active chemical molecules. A number of publications disclose organic compounds derived from marine soft corals including Scheuer, P. J. (ed.) *Marine Natural Products, Chemical and Biological Perspectives,* Academic Press, New York, 1978–1983, Vol. I–V; Faulkner, D. J. (2002) *Nat. Prod. Rep.* 19:1–48; Faulkner, D. J. *Nat Prod Rep.* (2001)18:1–49; Faulkner, D. J. (2000); *Nat. Prod. Rep* 17:7–55; Long B H, Carboni J M, Wasserman A J, Cornell L A, Casazza A M, Jensen P R, Lindel T, Fenical W, Fairchild C R. (1998) "Eleutherobin, a novel cytotoxic agent that induces tubulin polymerization, is similar to paclitaxel (Taxol).*Cancer Res* 58:1111–5.

Marine soft corals have been the source of a number of natural pregnene analogs. For example: Pregna-5,20-dien-3-ol has been isolated from the soft coral *Gersemia rubiformis* Kingston, J. F.; Gregory, B.; Fallis, A. G., *J. Chem. Soc., Perkin Trans. I* 1979, 1, 2064. Pregna-5,20-dien-3-ol-β-D-Galactopyranoside has been isolated from the gorgonian coral of the genus *Pseudoplexaura waagenaari* (Wasylyk, J. M.; Martin, G. E.; Weinheimer, A. J.; Alam, M. *J. Nat. Prod.* 1989, 52, 391) 18-acetoxypregna-1,4,20-trien-3-one, has been reported from the soft coral *Telesto riseii* Ross, R. A.; Scheuer, P. J. *Tetrahedron Lett.* 1979, 4701; 11-acetoxypregna-4,20-dien-3-one from the gorgonian *Eunicella cavolini* (Cimino, G.; Desiderio, B.; De Stefano, S.; Sodano, G. *Experientia* 1978, 35, 298) and 3-O-(4-O-acetyl-alpha-L-fucopyranoside) from a gorgonian Eunicea sp. (Cobar, O. M. Rodriguez A. D., Padilla, O. L., *J. Nat. Prod.* 1997, 60, 1186–1188).

BRIEF SUMMARY OF THE INVENTION

A principal object of the subject invention is the provision of novel compositions of biologically active compounds which have utility for use in promoting apoptosis and inhibiting cellular proliferation. In a specific embodiment, the compounds and compositions of the subject invention can be used in the treatment of cancer.

One aspect of the current invention concerns the novel compound Swiftiapregnene (I). Advantageously, Swiftiapregnene can inhibit unwanted cellular proliferation, including the proliferation of tumor cells.

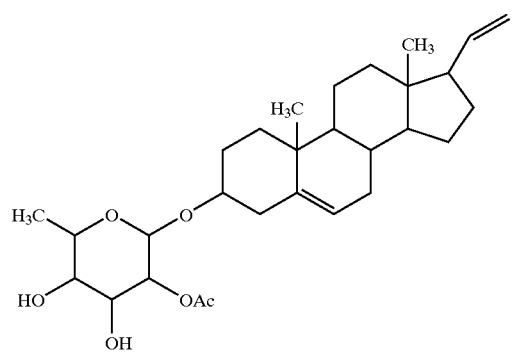

Swiftiapregnene (I)

In a specific embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. The mechanisms for achieving anticancer activity exhibited by the subject compounds would lead a person of ordinary skill in the art to recognize the applicability of the subject compounds, compositions, and methods to additional types of cancer as described herein.

In specific embodiments, the subject invention provides new glycosylated pregnenes, as exemplified by Swiftiapregnene (I). Swiftiapregnene has not been isolated previously from a natural source nor have they been previously synthesized.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

Figure 1A:
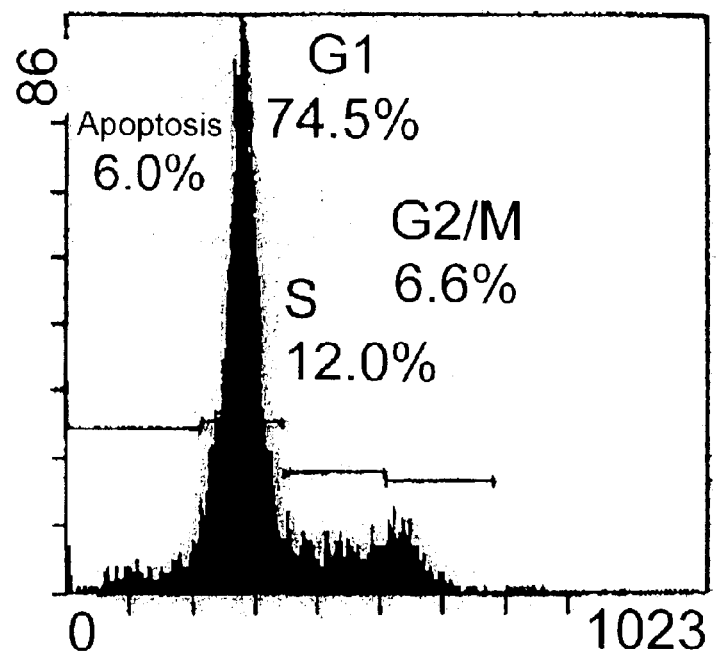
FIGS. 1A–B shows flow cytometric histograms showing cell cycle effects on untreated vs. treated A549 human lung adenocarcinoma cells.

(1A)—shows untreated control cells;

(1B)—shows cells treated with 100 ug/ml Swiftiapregnene (I);

DETAILED DISCLOSURE OF THE INVENTION

The subject invention provides novel compositions of biologically active pregnene compounds which are useful for inducing apoptosis and/or inhibiting pathological cellular proliferation. In a preferred embodiment, these compounds can be used for treating cancer. More specifically, the novel compounds, compositions and methods of use can advantageously be used to inhibit the growth of tumor and other cancer cells in a mammalian host. As described herein, the compounds of the subject invention have utility for use in the treatment of cancer. More particularly, the subject compounds can be used for inhibiting in a human the growth of tumor cells, including cells of breast, prostate, colon, CNS, ovarian, renal, liver, pancreatic, uterine, or lung tumors, as well as human leukemia or melanoma cells. The compounds also have utility in the treatment of multi-drug resistant cancer cells.

In a preferred embodiment, the subject invention provides compounds having the following formula:

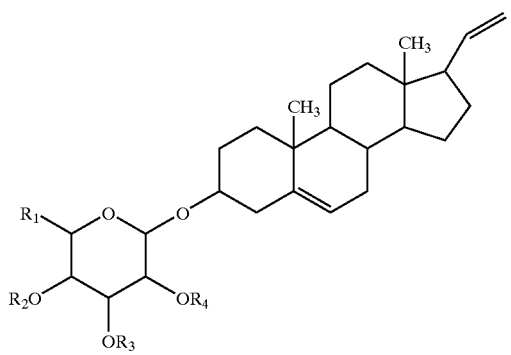

wherein $R_1$=CH$_3$, CH$_3$ CH$_2$OH or CH$_2$OAc;

$R_2$=H or C1–C6 alkyl;

$R_3$=H, Ac or C1–C6 alkyl; and $R_4$=H, Ac or C1–C6 alkyl.

In specific embodiments, the subject invention provides Swiftiapregnene (I) having the following structure:

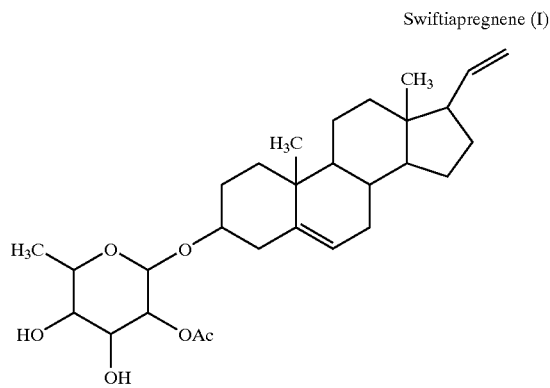

Swiftiapregnene (I)

In a further specific embodiment, the subject invention provides the following compound:

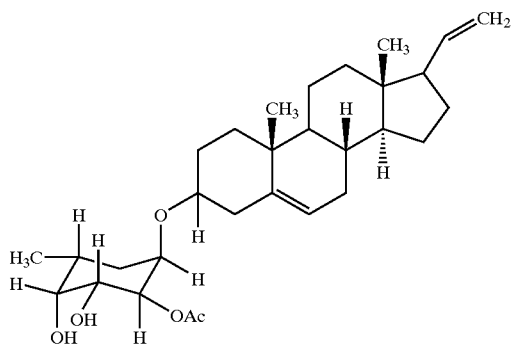

In a particularly preferred embodiment the compound of the subject invention has the following structure:

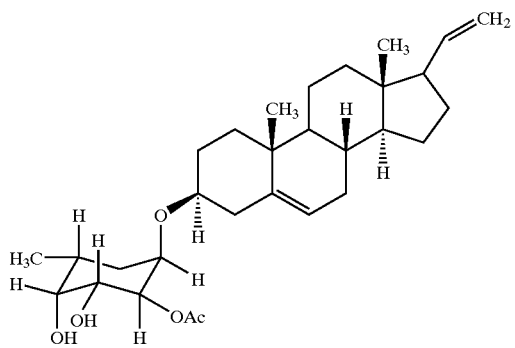

In accordance with the subject invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

The subject invention further provides methods of use of the new compounds and compositions of the invention, e.g., methods of inhibiting tumors and other cancer cells in an animal, preferably a mammal. Most preferably, the invention comprises a method for the antitumor treatment of a human in need of such treatment, i.e., a human hosting cancer cells, including breast, colon, liver, pancreatic, uterine, or lung tumor cells, or leukemia cells including multi-drug resistant cancer cells.

In preferred embodiments of the invention, the compounds are substantially pure, i.e., contain at least 95% of the compound as determined by established analytical methods.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Isolation and Structure Elucidation of Swiftiapregnene (I)

A. Collection and Taxonomy of the Source Organism

This gorgonian specimen (HBOI ID #13-VIII-95-4-001) was collected using an otter trawl in the Gulf of Mexico, ~85 nmi southwest of Sanibel, Fla., 26°15.760'N latitude and 83°42.947'W longitude, and at a depth of 74 m. The sample was frozen at −20° C. until work up. A museum voucher specimen is deposited at the Harbor Branch Oceanographic Museum, catalog number 012:00805.

The specimen most closely fits the description of *Swiftia exerta* (Ellis & Solander, 1786) in Deichmann, 1936 [Cnidaria, Anthozoa, Gorgonacea, Plexauridac (Paramuriceidae)]. This holaxonian gorgonian specimen was ~130 cm tall, ~120 cm wide, and branching in one plane. The base of the main stem is ~3 cm in diameter and has 4 primary branches; the terminal branchlets diverge at nearly a 90° angle. The calyces are closely distributed over the entire surface, conical ~1 mm tall, and the polyps are exert. The spicules of the coenenchyme consist of spiny spindles ~0.20–0.55 mm in length and capstans ~0.08–0.10 mm. The anthocodial spicules are slightly spiny spindles ~0.50–0.60 mm in length. The axis is soft and fibrous. The live specimen was bright red-orange; in alcohol the specimen is cream-white.

B. Isolation of Swiftiapregnene (I)

100 g of the frozen gorgonian, *Swiftia exerta,* was finely chopped and then ground using a Waring blender in the presence of ethanol (Pharmco 100%). The extract was filtered and the tissue returned to the blender and ground again with ethanol (500 ml). The latter step was repeated two additional times. The filtrate was concentrated by distillation under reduced pressure to yield 6.2 g of an oily residue. This material was suspended in ethyl acetate (100 ml) and water (100 ml) and then extracted repeatedly with ethyl acetate (3×100 ml) to provide after combination and concentration by distillation under reduced pressure, a non-polar ethyl acetate extract (3.17 g). This non-polar ethyl acetate extract was chromatographed by vacuum column chromatography using a step gradient of ethyl acetate in heptane followed by methanol in ethyl acetate. The column was eluted with: Fraction 1: heptane-ethyl acetate 8:2 (v/v) 150 ml; Fraction 2: heptane-ethyl acetate 6:4 (v/v) 150 ml; Fraction 3: heptane-ethyl acetate 4:6 (v/v) 150 ml; Fraction 4: heptane-ethyl acetate 2:8 (v/v) 150 ml; Fraction 5: ethyl acetate 150 ml; Fraction 6: ethyl acetate-methanol 25:75 (v/v) 150 ml; Fraction 7: 100% methanol 150 ml. Fraction 4 was further purified by preparative thin layer chromatography on a silica gel stationary phase (EM SCIENCE PLATE#). The plate was eluted with methanol-dichloromethane (5:95 v/v). Bands were detected by spraying a portion with 2% vanillin in sulfuric acid followed by heating. Bands were scraped off the plate, soaked in 25% methanol in dichloromethane for 20 minutes and then filtered to remove the silica gel. All visible bands were scraped off the plate and then analyzed by NMR. Swiftiapregnene had an RF of approximately 0.28 under these conditions. This RF was variable dependent upon loading of the plate. After concentration by distillation under reduced pressure, 7 mg of Swiftiapregnene (I) was obtained. Swiftiapregnene (I): colorless oil. See Table 1 for $^1H$ and $^{13}C$ NMR data.

TABLE 1

NMR Data for swiftiapregnene (I)

| Atom # | | $^1H$ NMR δ (mult. J in Hz) | $^{13}C$ NMR δ (mult. J in Hz) | |
|---|---|---|---|---|
| 1 | A | 1.11 (m) | 38.20 | t |
|   | B | 1.88 (m) | | |
| 2 | A | 1.56 (m) | 30.47 | t |
|   | B | 1.86 (m) | | |
| 3 |   | 3.36 (m) | 78.07 | d |
| 4 | A | 2.15 (ddd, 11.8, 11.8, 1.5) | 39.42 | t |
|   | B | 2.26 (dd 11.8, 2.7) | | |
| 5 |   | — | 141.47 | s |
| 6 |   | 5.35 (bs) | 122.32 | d |
| 7 | A | 1.56 (m) | 32.69 | t |
|   | B | 2.03 (m) | | |
| 8 |   | 2.01 (m) | 32.85 | d |
| 9 |   | 0.98 (m) | 51.46 | d |
| 10 |   | | 37.58 | s |
| 11 | A | 1.45 (m) | 21.40 | t |
|    | B | 1.61 (m) | | |
| 12 | A | 1.11 (m) | 38.17 | t |
|    | B | 1.7 (m) | | |
| 13 |   | | 44.08 | s |
| 14 |   | 1.03 (m) | 56.73 | d |
| 15 | A | 1.23 (m) | 27.88 | t |
|    | B | 1.69 (m) | | |
| 16 | A | 1.58 (m) | 25.47 | t |
|    | B | 1.77 (m) | | |
| 17 |   | 1.98 (m) | 56.21 | d |
| 18 |   | 0.63 (3H, s) | 13.07 | q |
| 19 |   | 1.03 (3H, s) | 19.74 | q |
| 20 |   | 5.76 (m) | 140.46 | d |
| 21 | A | 4.96 (d 5.0) | 115.00 | t |
|    | B | 4.94 (s) | | |
| 1' |   | 5.05 (d 3.7) | 95.67 | d |
| 2' |   | 4.86 (dd 10.1, 3.7) | 72.48 | d |
| 3' |   | 3.94 (dd 10.1, 2.1) | 68.49 | d |

TABLE 1-continued

NMR Data for swiftiapregnene (I)

| Atom # | $^1$H NMR δ (mult. J in Hz) | $^{13}$C NMR δ (mult. J in Hz) | |
|---|---|---|---|
| 4' | 3.75 (bs) | 73.09 | d |
| 5' | 4.04 (dd) | 66.83 | d |
| 6' | 1.18 (3H, d 6.4) | 16.64 | q |
| OCOCH3 | 2.01 (3H, s) | 20.93 | q |
| OCOCH3 | | 171.20 | s |

EXAMPLE 2

Antiproliferative Effects of Enriched Fractions Containing Swiftiapregnene (I) on Cell Division in Fertilized Sea Urchin Eggs Assays were run as per the protocols described by Jacobs S. R., White, S and Wilson L. (1981). ("Selective Compounds Derived from Marine Organisms: Effects on Cell Division in Fertilized Sea Urchin Eggs." *Federation of American Societies for Experimental Biology*, 40, 2212–2222). Briefly, urchins *Arbacia punctulata* were collected off Fort Pierce, Fla., on the near shore shallow reef. Male and female urchins are induced to spawn by the injection of 0.1–0.3 ml of 0.5 M KCL through the soft tissue of the oral surface into the coelomic cavity. The gametes emerged through the aboral surface and the red eggs are collected into a beaker containing a small amount of ASW by inverting the urchin. These eggs are pipetted into a centrifuge tube and hand centrifuged to determine the total volume of packed eggs. ASW is then added to yield a final concentration of ~1% egg slurry in ASW. The white sperm are collected "dry" using a Pasteur pipette and stored in a capped test tube suspended on ice. A solution of 50 μl of "dry" sperm in 25 ml of ASW was prepared to use in the assay. 1–3 μl of the sperm suspension is added to the egg slurry. Fertilization occurred within 60–90 seconds and was evident through the appearance of a fertilization membrane observed by the IMT-2 Olympus microscope (150× magnification).

24-well plates (Falcon) are preloaded with 500 μl of ASW and 10 μl of test substance at 10 mg/ml in ethanol. After 5–10 minutes. 500 μl of the fertilized dispersed egg suspension was added to each sample well. The cells are incubated at room temperature for 1.5 hours, at which time the control embryos have reached the 2 or 4 cell stage. The microscope is used to observed division, inhibition or deformation. The total number of cells that have divided, that did not divide or that showed deformation are recorded. The percent inhibition is the percentage of cells compared to control that had not divided at the time of scoring. Samples were assayed in triplicate and three fields scored. The value for each well is averaged across all three wells.

Fraction 4 from the chromatography above was tested for its ability to inhibit cell division in this model. This fraction, which is 90% Swiftiapregnene (I), showed 100% inhibition of fertilized sea urchin cell division at a concentration of 100 μg/ml.

EXAMPLE 3

Antitumor Effects of Swiftiapregnene (I)

A. Effects of Swiftiapregnene on In Vitro Proliferation of Tumor Cell Lines

Swiftiapregnene was analyzed as to its effect on the proliferation of PANC-1 human pancreatic and P388 murine leukemia cell lines. P388 cells were obtained from Dr. R. Camalier, National Cancer Institute, Bethesda, Md., and PANC-1 cells were obtained from American Type Culture Collection, Rockville, Md. All cell lines were maintained in tissue culture medium (TCM; Roswell Park Memorial Institute RPMI 1640 supplemented with 100 U/mL penicillin, 100 mg/mL streptomycin, 60 mg/mL 1-glutamine, 18 mM HEPES, 0.05 mg/mL gentamicin (Life Technologies, Gaithersburg, Md.) and 10% fetal bovine serum) and cultured in plastic tissue culture flasks at 37° C. in humidified air containing 5% $CO_2$. Stock cultures of P388 cells were subcultured 1:20 in fresh TCM every 2 to 3 days. Stock cultures of A549 cells were subcultured 1:10 every 3 to 4 days. To assess the antiproliferative effects of agents against the cells, 200 mL cultures (96-well tissue culture plates, Nunc, Denmark) were established at 1×10$^5$ cells/mL in TCM or TCM containing the test agent at 0.03–5.0 μg/mL. After 48-h exposures, P388 cells were enumerated using 3-[4,5-dimethylthiazol-2-yl]-2,5-diphenyltetrazolium bromide (MTT) as described in the literature (M. C. Alley, et al., Cancer Res. 48:589, 1988). PANC-1 cells were enumerated in the same manner after 72 hours exposure. The results were expressed as percent inhibition compared to the negative (no drug) control. Positive drug controls of varying dilutions of 5-fluorouracil and adriamycin (Sigma Chemical Co., St Louis, Mo.) were included to monitor drug sensitivity of the cell line.

To quantitate the effects on cell proliferation and resulting $IC_{50}$ values, 75 mL of warm growth media containing 5 mg/mL MTT is added to each well, cultures returned to the incubator, and left undisturbed for 3 hours. To spectrophotometrically quantitate formation of reduced formazan, plates are centrifuged (500×g, 10 minutes), culture fluids removed by aspiration, and 200 μl of acidified isopropanol (2 mL concentrated HCl/liter isopropanol) added per well. The absorbance of the resulting solutions is measured in a plate reader (TECAN Spectra SLT; TECAN U.S., Research Triangle Park, N.C.) at 570 nm and a 650 nm reference filter. The absorbance of test wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp.316–348, Charles Griffin Co., London, 1978). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination.

A summary of results in these assays for compound I can be found in Table 2.

TABLE 2

| | PANC-1 (IC$_{50}$ µg/ml) | P388 (IC$_{50}$ µg/ml) |
|---|---|---|
| Swiftiapregnene (I) | 7.4 | 21 |

B. Effect of Swiftiapregnene on Cell Cycle Progression of A549 Human Lung Cells

Cell cycle studies were initiated in order to pinpoint a specific phase within the cell cycle in which discodermolide analogs were exerting their antiproliferative effect. A549 human lung cells were used as cell cycle targets to compare the effects of discodermolide and discodermolide analogs on perturbation of the cell cycle. Cell cycle analyses were performed as follows: A549 cells were incubated at 37° C. in 5% CO$_2$ in air in the presence or absence of varying concentrations of discodermolide or discodermolide analogs for 24 hr. Cells were harvested, fixed in ethanol, washed, and stained with 0.2 mg/mL of propidium iodide (P.I.) together with 0.1 mg/mL of RNAse A. Stained preparations were analyzed on a Coulter EPICS ELITE flow cytometer with 488 nM excitation. Fluorescence measurements and resulting DNA histograms were collected from at least 10,000 P.I. stained cells at an emission wavelength of 690 nM. Raw histogram data was further analyzed using a cell cycle analysis program (Multicycle, Phoenix Flow Systems).

Figure 1B:
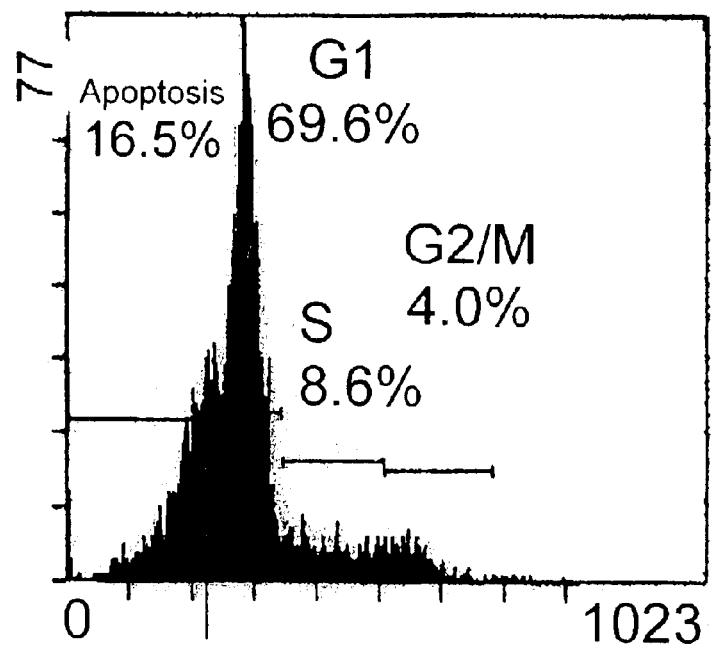

FIGS. 1A–B show control (untreated) A549 cells and A549 cells treated with 100 µg/ml Swiftiapregnene. Swiftiapregnene (I) causes an increase in the sub-G1 population indicating an increase in cells which have undergone apoptosis.

EXAMPLE 4

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated compound having the following structural formula:

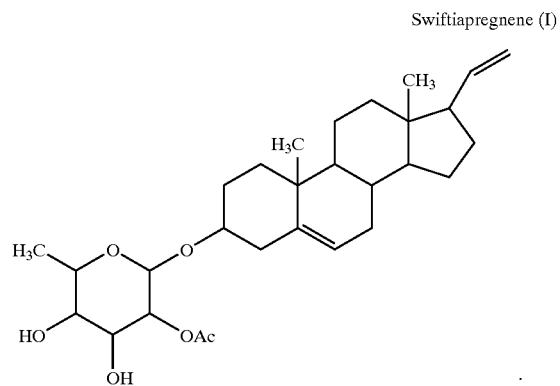

Swiftiapregnene (I)

2. The compound, according to claim 1, wherein said compound has the following structure:

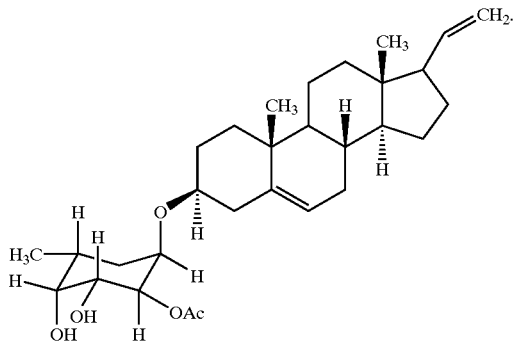

3. The compound, according to claim 1, having the following NMR spectral data: $^{13}$C (observed at 125 MHz in d6-acetone) 171.2 s, 141.5 s, 140.5 d, 122.3 d, 115.0 t, 95.7 d, 78.1 d, 73.1 d, 72.5 d, 68.5 d, 66.8 d, 56.7 d, 56.2 d, 51.5 d, 44.1 s, 39.4 t, 38.2 t, 38.2 t, 37.6 s, 32.8 d, 32.7 t, 30.5 t, 27.9 t, 25.5 t, 21.4 t, 20.9 q, 19.7 q, 16.6 q, 13.1 q; $^1$H (observed at 500 MHz in d6-acetone) 5.76 (m), 5.35 (bs), 5.05 (d 3.7), 4.96 (d 5.0), 4.94 (s), 4.86 (dd 10.1, 3.7), 4.04 (q 6.45), 3.94 (dd 10.1, 2.1), 3.75 (bs), 3.36 (m), 2.26 (dd 11.8, 2.7), 2.15 (ddd 11.8, 11.8, 1.5) 2.03 (m), 2.01 (m), 2.01 (3H, s), 1.98 (m), 1.88 (m), 1.86 (m), 1.77 (m), 1.7 (m), 1.69 (m), 1.61 (m), 1.58 (m), 1.56 (m), 1.56 (m), 1.45 (m), 123 (m), 1.18 (3H, d 6.4), 1.11 (m), 1.11 (m), 1.03 (m), 1.03 (3H, s), 0.98 (m), 0.63 (3H, s).

4. A method for inhibiting cancer cell proliferation, said method comprising administering to a patient in need of such treatment an effective amount of a compound having the following structure:

Swiftiapregnene (I)

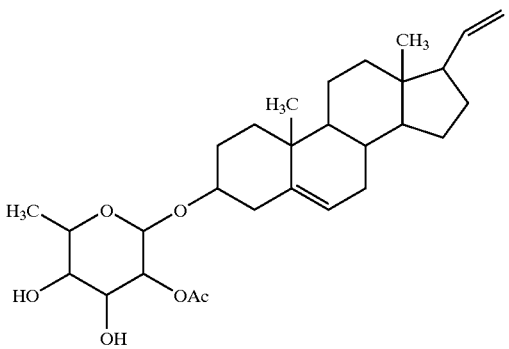

5. The method, according to claim 4, wherein said compound has the following structure:

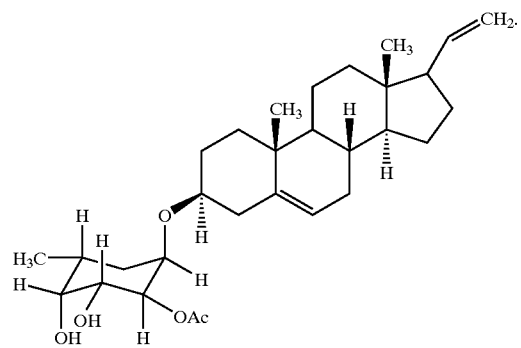

6. The method, according to claim 4, wherein said compound has the following NMR data: $^{13}$C (observed 125 MHz in d6-acetone) 171.2 s, 141.5 s, 140.5 d, 122.3 d, 115.0 t, 95.7 d, 78.1 d, 73.1 d, 72.5 d, 68.5 d, 66.8 d, 56.7 d, 56.2 d, 51.5 d, 44.1 s, 39.4 t, 38.2 t, 38.2 t, 37.6 s, 32.8 d, 32.7 t, 30.5 t, 27.9 t, 25.5 t, 21.4 t, 20.9 q, 19.7 q, 16.6 q, 13.1 q; $^1$H (observed at 500 MHz in d6-acetone) 5.76 (m), 5.35 (bs), 5.05 (d 3.7), 4.96 (d 5.0), 4.94 (s), 4.86 (dd 10.1, 3.7), 4.04 (q 6.45), 3.94 (dd 10.1, 2.1), 3.75 (bs), 3.36 (m), 2.26 (dd 11.8, 2.7), 2.15 (ddd 11.8, 11.8, 1.5) 2.03 (m), 2.01 (m), 2.01 (3H, s), 1.98 (m), 1.88 (m), 1.86 (m), 1.77 (m), 1.7 (m), 1.69 (m), 1.61 (m), 1.58 (m), 1.56 (m), 1.56 (m), 1.45 (m), 123 (m), 1.18 (3H, d 6.4), 1.11 (m), 1.11 (m), 1.03 (m), 1.03 (3H, s), 0.98 (m), 0.63 (3H, s).

7. A pharmaceutical composition comprising a pharmaceutical carrier and an isolated compound having the following structure:

Swiftiapregnene (I)

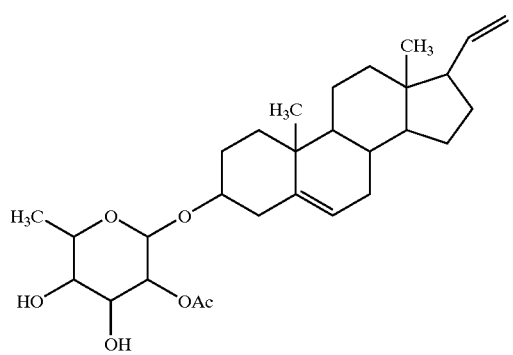

8. The pharmaceutical composition, according to claim 7, wherein said compound has the following structure:

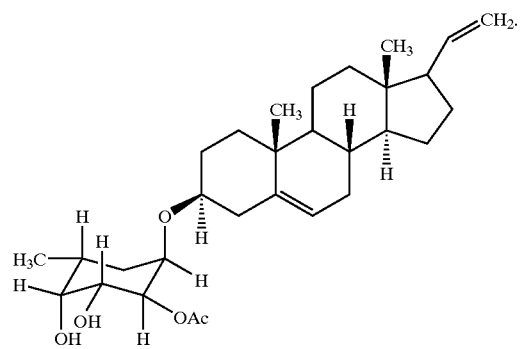

9. The pharmaceutical composition, according to claim 7, wherein said compound has the following NMR spectral data: $^{13}$C (observed at 125 MHz in d6-acetone) 171.2 s, 141.5 s, 140.5 d, 122.3 d, 115.0 t, 95.7 d, 78.1 d, 73.1 d, 72.5 d, 68.5 d, 66.8 d, 56.7 d, 56.2 d, 51.5 d, 44.1 s, 39.4 t, 38.2 t, 38.2 t, 37.6 s, 32.8 d, 32.7 t, 30.5 t, 27.9 t, 25.5 t, 21.4 t, 20.9 q, 19.7 q, 16.6 q, 13.1 q; $^1$H (observed at 500 MHz in d6-acetone) 5.76 (m), 5.35 (bs), 5.05 (d 3.7), 4.96 (d 5.0), 4.94 (s), 4.86 (dd 10.1, 3.7), 4.04 (q 6.45), 3.94 (dd 10.1, 2.1), 3.75 (bs), 3.36 (m), 2.26 (dd 11.8, 2.7), 2.15 (ddd 11.8, 11.8, 1.5) 2.03 (m), 2.01 (m), 2.01 (3H, s), 1.98 (m), 1.88 (m), 1.86 (m), 1.77 (m), 1.7 (m), 1.69 (m), 1.61 (m), 1.58 (m), 1.56 (m), 1.56 (m), 1.45 (m), 123 (m), 1.18 (3H, d 6.4), 1.11 (m), 1.11 (m), 1.03 (m), 1.03 (3H, s), 0.98 (m), 0.63 (3H, s).

\* \* \* \* \*

UNITED STATES PATENT AND TRADEMARK OFFICE
CERTIFICATE OF CORRECTION

PATENT NO. : 6,784,160 B1
DATED : August 31, 2004
INVENTOR(S) : Amy E. Wright, John K. Reed and Ross E. Longley It is certified that error appears in the above-identified patent and that said Letters Patent is hereby corrected as shown below:

Column 5,
Line 47, "Plexauridac" should read -- Plexauridae --.

Column 11,
Lines 36-37, "123 (m)," should read -- 1.23 (m) --.

Column 12,
Lines 28-29, "123 (m)," should read -- 1.23 (m) --.

Column 14,
Line 4, "123 (m)," should read -- 1.23 (m) --.

Signed and Sealed this

Fifth Day of April, 2005

JON W. DUDAS
*Director of the United States Patent and Trademark Office*